US006426325B1

(12) United States Patent
Dente et al.

(10) Patent No.: US 6,426,325 B1
(45) Date of Patent: Jul. 30, 2002

(54) FRAGRANCE COMPOSITIONS

(75) Inventors: Stephen V. Dente, Tenafly; William Weston, Wayne, both of NJ (US)

(73) Assignee: Robertet Fragrances, Oakland, NJ (US)

( * ) Notice: Subject to any disclaimer, the term of this patent is extended or adjusted under 35 U.S.C. 154(b) by 0 days.

(21) Appl. No.: 09/717,412

(22) Filed: Nov. 21, 2000

(51) Int. Cl.$^7$ ................................................. C11D 7/10
(52) U.S. Cl. ........................... 510/101; 512/4; 424/76.4
(58) Field of Search ................................. 510/101, 441, 510/442; 424/76.4; 512/4

(56) References Cited

U.S. PATENT DOCUMENTS

| | | | |
|---|---|---|---|
| 3,921,581 A | | 11/1975 | Brewer |
| 4,020,156 A | | 4/1977 | Murray et al. |
| 4,110,261 A | | 8/1978 | Newland |
| 4,209,417 A | | 6/1980 | Whyte |
| 4,225,444 A | | 9/1980 | Schmitt |
| 4,267,166 A | | 5/1981 | Yajima |
| 4,536,315 A | | 8/1985 | Ramachandran et al. |
| 4,904,639 A | | 2/1990 | Hallam |
| 4,929,378 A | * | 5/1990 | Morita et al. ................ 252/105 |
| 5,000,869 A | * | 3/1991 | Dittert ................... 252/174.13 |
| 5,041,421 A | * | 8/1991 | King ............................. 512/4 |
| 5,614,179 A | * | 3/1997 | Murphy et al. ............... 424/65 |

FOREIGN PATENT DOCUMENTS

EP   0 381 529 A2   8/1990

OTHER PUBLICATIONS

Cargill Foods Technical Information, "Premier Extra Coarse Flake Salt", No. 22.1 WG, 1995.
Cargill Foods Technical Information, "Alberger Flake Topping Salt", No. 1040, 1999.
Cargill Foods Technical Information, "Alberger Flake Salt", No. 1015, 1999.
Cargill Foods Technical Information, "Alberger Special Flake Salt", No. 1020, 1999.
Cargill Foods Technical, "Microsized 66 Fine Salt", No. 3251, 1999.
Cargill Salts Technical Information, No. PD 5411A 1997.
Morton Salt Product Data, "White Crystal Southern Rock Salt Extra Coarse, Coarse, Medium", PDS 201.2, Dec. 1992.

* cited by examiner

*Primary Examiner*—John Hardee
(74) *Attorney, Agent, or Firm*—Mathews, Collins, Shepherd & McKay, P.A.

(57) ABSTRACT

A dry fragrance composition having from about 0.1 to about 20%, by total carrier weight, of a fragrance composition substantially uniformly deposited on the surface of a nonabsorbent solid inorganic particulate substrate is used to impart a fragrance to a second material. The nonabsorbent solid inorganic particulate substrate can be an alkali metal chloride, sulfates, or tripolyphosphates, soda ash, borax, or a zeolite.

10 Claims, No Drawings

FRAGRANCE COMPOSITIONS

The present invention relates to a dry fragrance composition for imparting a fragrance to a second particulate material through physical admixture.

BACKGROUND OF THE INVENTION

U.S. Pat. No. 4,020,156 to Murray discloses a fragrant bead composition with a multiplicity of prilled urea beads. The beads have an adherent surface coating consisting essentially of finely divided particles of calcium silicate, magnesium carbonate, or silicon dioxide, and dextrin as a binder. The particles have a surface area of from about 80 to about 400 square meters per gram and contain a fragrance. The adsorbent is present in a ratio of from about 1 to 5 parts per 100 parts by weight of urea and in the coating in a ratio of about 0.2 to 2 parts per part by weight of dextrin; the fragrance is present in a ratio of from 1 to 3 parts per part by weight of adsorbent.

U.S. Pat. No. 4,110,261 to Newland, discloses a molding composition of petroleum wax and a synthetic polymer with a molecular weight below 10,000 and about 15% of a fragrance. In one embodiment, this constitutes a shell about an unperfumed core of wax.

U.S. Pat. No. 4,209,417 to Whyte discloses perfumed particles having a continuous water-soluble polymer matrix in which there is uniformly dispersed perfume/emulsifier droplets. Droplets on the surface give an immediate perfume effect while droplets below the surface give a sustained release perfume. The droplets within the matrix are released upon contact with water. The perfumed particles have a particle size of from 40 microns to 1400 microns, preferably 175 microns to 1000 microns while the perfume/emulsifier droplets have diameters of from 0.01 microns to 0.5 microns.

U.S. Pat. No. 4,225,444 to Schmitt discloses butanoyl cyclohexane derivatives as a perfume which can be used in various compositions (soaps, space odorants and deodorants, colognes, toilet water, bath preparations etc.) including powders such as talcs, dusting powders, face powders and the like. The perfume composition or fragrance composition can contain a vehicle, or carrier such as a liquid such (a nontoxic alcohol or glycol such as propylene glycol) or an absorbent solid, such as gum (such as gum arabic or gelatin).

U.S. Pat. No. 4,267,166 to Yajima discloses a composition (edible particles, an edible troche, an edible liquid, chewing gum or toothpaste) for treating bad breath with from 0.5 to 50% by weight of cyclodextrin and an edible carrier for oral administration.

U.S. Pat. No. 4,904,639 to Hallam discloses an air freshener having a homogenized mixture of polyethylene glycol and water as a plasticizing agent with a perfume incorporated therein. The air freshener is made by mixing particulate solid polyethylene glycol with a plasticizing amount of water to form a slurry, heating, and agitating the slurry until it is homogenized, adding a perfume to the homogenized material while agitating to disperse the perfume, and solidifying the composition so that the perfume is dispersed throughout.

U.S. Pat. No. 5,041,421 to King discloses a fragrance having discrete pellets of compressed salt, typically sodium chloride, with a fragrant oil dispersed within the pellets. The compressed salt is disclosed as being odorless, nonflammable, nontoxic, nonallergenic, nonnutritive, environmentally safe, homogeneous, non-crumbling with a high pressure break strength, and does not melt even at elevated temperatures. The fragrance is uniformly dispersed throughout the pellets, a feature which is said to be beneficial since the composition has no surface film.

It also is generally known that particulate materials such as soaps and detergents are spray dried to remove moisture. Typically, however, the addition of a fragrance is accomplished by spraying, thereby reintroducing moisture into the spray dried material and requiring another mixing operation.

DETAILED DESCRIPTION

The dry fragrance composition of the present invention utilizes a nonabsorbent solid inorganic particulate substrate on the surface of which is substantially uniformly deposited a fragrance. The resulting fragrance composition can be used to impart a fragrance to a second particulate material, such as laundry detergents, automatic dishwasher detergents, animal litter, bath salts, carpet cleaners, rug and room deodorizers, fabric bleaches, powdered cleaners, fabric softeners, and the like, through simple physical admixture and without the need to wet or moisten the second particulate material. The fragrance and formulation of powdered, granulated, and dry blended products can thus be enhanced. The final products can be formulated as powders or in the form of unit dose, tablet, pouch, gelcap, and the like, Moreover, when the fragrance is applied to the surface of the nonabsorbent solid inorganic particulate substrate, as opposed to being dispersed in and/or throughout the second particulate material, an increase in fragrance strength and performance can be discerned, meaning that less fragrance need be added. Manufacturing is also simplified and waste is reduced since addition is more controlled and does not require spraying while at the same time the stability of the fragrance in the finished product is improved.

The nonabsorbent solid inorganic particulate substrate will be inert to the second particulate material, that is to the material to which it is to be added. Suitable nonabsorbent solid inorganic particulate substrates include alkali metal chlorides, sulfates, or tripolyphosphates, soda ash, borax, and zeolites. Preferably the nonabsorbent solid inorganic particulate substrate is sodium chloride. Combinations of nonabsorbent solid inorganic particulate substrates can be used.

Ideally the density and particle size of the nonabsorbent solid inorganic particulate substrate is selected so as to approximate the density and particle size of the second particulate material, thereby facilitating maintenance of product homogeniety. A wide variety of particle sizes for the nonabsorbent solid inorganic particulate substrates can be employed, ranging from a mesh size of from about 400 to about 10.

The amount of fragrance carried by the nonabsorbent solid inorganic particulate substrate will vary with the substrate but flowability can be readily controlled. Thus if with a given fragrance level a drier, more flowing composition is desired, a moisture absorbing material such as zeolite can be added to the nonabsorbent solid inorganic particulate substrates carrying the fragrance until the desired flowability is obtained.

The term "fragrance" as used herein refers to any odoriferous material having a vapor pressure below atmospheric pressure at ambient temperatures. The fragrance material will most often be liquid at ambient temperatures. A wide variety of chemicals are known for fragrance uses, including materials such as aldehydes, ketones, and esters. More commonly, naturally occurring plant and animal oils and exudates comprising complex mixtures of various chemical components are known for use as fragrances. The fragrances herein can be relatively simple in their composition or can comprise highly sophisticated complex mixtures of natural and synthetic chemical components, all chosen to provide any desired odor. Typical fragrances can comprise, for example, woody/earthy bases containing exotic materials such as sandalwood oil, civet and patchouli oil. The fragrances can be of a light floral fragrance, e.g. rose extract, violet extract, and lilac. The fragrances can also be formulated to provide desirable fruity odors, e.g. lime, lemon and orange. Any material which exudes a pleasant or otherwise desirable odor can be used in the present invention.

The fragrance composition is deposited on the surface of the nonabsorbent solid inorganic particulate substrate so that there is from about 0.1% to about 30%, by total carrier weight of the fragrance composition, preferably from about 1% to about 20%. Preferably there is from about 4 to about 15%, by total carrier weight of the fragrance composition. The actual fragrance component of the fragrance composition typically will be oils of organic nature having different volatilities, many of which are commercially available. Typical fragrant oils are set forth in the Kirk-Othmer Encyclopedia of ChemicalTechnology, 14, 2d. (1967). The particular oil selected is not critical and is a matter of choice.

The fragrance composition also can provide a visual clue, that is, it can include a coloring agent. Typically this will be a dye that is compatible with the fragrance composition. In one embodiment, the color of the fragrance composition is selected so as to contrast with the color of the second particulate material, thereby making the presence of fragrance composition visibly discernable in the second particulate material. The particular color selected, however, also is not critical and is a matter of choice.

The dry fragrance composition is prepared by mixing the selected nonabsorbent solid inorganic particulate substrate with fragrance and any coloring material. The dry fragrance composition then can be stored or shipped for subsequent mixing with a second particulate material such as a detergent.

In long term testing, the fragrance strength remains high, demonstrating both an affinity of the fragrance for the nonabsorbent solid inorganic particulate substrate and the absence of any appreciable migration to the second particulate material.

A further aspect of the invention provides for a uniform admixture of (a) a particulate material such as laundry detergents, automatic dishwasher detergents, animal litter, bath salts, carpet cleaners, rug and room deodorizers, fabric bleaches, and powdered cleaners, and (b) a quantity of a dry fragrance composition having (i) a nonabsorbent solid inorganic particulate substrate which is inert to the particulate material and consisting essentially of sodium chloride, and (ii) from about 0.1 to about 30%, by weight of the composition, of a fragrance composition substantially uniformly deposited on its surface which is sufficient to impart the fragrance to the particulate material.

Thus the present compositions are especially useful, but by no means exclusively useful, when admixed with detergent composition. Detergent compositions contain a water-soluble organic surfactant and detergency adjunct materials in addition to the dry fragrance composition. The level of surfactant depends upon the type of detergency product, but generally ranges from 0.05% to 35%. The organic surfactants can be anionic surfactants, nonionic surfactants, ampholytic surfactants, zwitterionic surfactants and mixtures thereof. The detergent composition can be a pre-soak detergent composition, main wash detergent composition, automatic dishwasher detergent, or a household cleaner detergent composition in any particulate, that is granular or powder, form. Pre-soak and household cleaner detergent compositions contain a low level of surfactant, primarily for dispersing the composition throughout the aqueous bath. A level of surfactant from 0.05% to 2%, preferably 0.25% to 1% is used. A main wash detergent composition contains from 5% to 35%, preferably 8% to 20% surfactant. The balance of the detergent composition can consist essentially of detergency adjunct materials such as a builder, soil suspending agent, processing aid, brightener, enzyme, bleach, and mixtures thereof. While the nature and amount of the adjunct materials will dependent on the use of the product, a typical detergent composition will be a built detergent composition containing from 10% to 80%, preferably 25% to 75% detergency builder. Other compositions are described by K. R. Lange in *Detergents and Cleaners*, Chapter 6, the disclosure of which is incorporated herein by reference. In each case, the dry fragrance composition described herein is admixed with these detergent compositions as herein described.

Other compositions with which the dry fragrance composition is advantageously mixed include animal litter, bath salts, carpet cleaners, rug deodorizers, room deodorizers, fabric bleaches, powdered cleaners, etc. Animal litters for example typically include a finely subdivided or powdered carrier having a powder size passing a 20 mesh standard size sieve. Such solid materials include cellulosic materials such as finely ground hay, husks, sawdust, excelsior, cereal hulls, corncobs, etc., or chlorophyll-containing agents such as ground grasses, ground alfalfa and the like. The finely subdivided solid also can be mineral such as aluminosilicates or clay, e.g., kaolinite, halloysite, attapulgipe, montmorillonite, vermiculite, or hectorite, silica, limestone, alumina, etc. Any of the solids can be acidified with an acid to provide a neutralization capacity. A binder and water-sensitive disentegrant such as clays with water expanding crystal lattices such as bentonite and vermiculite, and water soluble or dispersible gums and polymers such as guar gum, microcrystalline cellulose and pregelatinized starches, also can be included. In each case, the dry fragrance composition described herein is admixed with these particulate materials.

The following examples will serve to further typify the nature of the invention but should not be construed as a limitation on the scope thereof, which is defined solely by the appended claims.

EXAMPLE 1

| Ingredient | Amount (%) |
|---|---|
| Sodium Chloride (Alberger Topping Salt; mesh 20 to 40) | 93.99 |
| Coloring Solution | 0.0048 |
| Floral Fragrance (Robertet PNT57) | 4.00 |

The coloring solution is formulated from 0.333 g. of FD&C Blue #1 and 9.4 g of water. This is sprayed on the sodium chloride particles with mixing. The fragrance is then sprayed on the surface of the particles, again with mixing, and the mixture stirred until a uniform color is obtained. Zeolite can be sprinkled on the mixture to facilitate the removal of any residual moisture.

EXAMPLE 2

Four parts of the fragrance on the nonabsorbent solid inorganic particulate substrate prepared as in Example 1 are mixed with 96 parts of unscented detergent and gently mixed for 5 minutes to provide a scented detergent composition.

EXAMPLE 3

A formulation similar to that described in Example 1 is prepared utilizing 93.99% sodium chloride (pretzel salt with mesh size of 10 to 40) and replacing the zeolite with a like amount of sodium tripolyphosphate.

EXAMPLE 4

Four parts of the fragrance composition prepared in Example 3 were mixed with 96 parts of unscented detergent and the two are gently mixed for 5 minutes to provide a scented detergent composition.

EXAMPLE 5

A formulation similar to that described in Example 3 is prepared substituting however 93.99% sodium chloride (Cargill Microsized salt with a mesh size through 325) utilized in detergent compositions.

EXAMPLE 6

A total of 97.5 parts of unscented detergent and 2.5 parts of the fragrance composition prepared in Example 5 were gently mixed for 5 minutes to provide a scented detergent composition.

EXAMPLE 7

A formulation suitable for providing a fragrance to conventional cat litter is prepared utilizing 90% sodium chloride, 5% sodium tripolyphosphate, and 5% fragrance in the manner described in Example 1.

EXAMPLE 8

| Ingredient | Amount (%) |
|---|---|
| Sodium Chloride | 84 |
| Sodium Bicarbonate | 9 |
| Sodium Tripolyphosphate (Powdered) | 6 |
| Fragrance | 1 |

The sodium bicarbonate is added to the sodium chloride particles with mixing. The fragrance is sprayed on the surface of the particles and the sodium tripolyphosphate powder is then added. The mixture is stirred until it is free-flowing.

EXAMPLE 9

Sixteen parts by weight of α-olefin sulfonate are added to 1000 parts by weight of the nonabsorbent solid inorganic particulate substrate prepared as in Example 8 and the mixture stirred for five minutes to produce a scented foaming bath product.

| Ingredient | Amount (%) |
|---|---|
| Sodium Tripolyphosphate Hexahydrate | 50 |
| Sodium Chloride | 35.5 |
| Sodium Tripolyphosphate (Powdered) | 5 |
| White Mineral Oil | 4 |
| Water | 2.5 |
| Caprylic Capric Trigyceride | 2 |
| Fragrance | 1 |

The water is sprayed on the sodium tripolyphosphate hexahydrate with mixing which is continued for 15 minutes. The mineral oil, caprylic capric trigyceride, and fragrance are mixed and sprayed on the surface of the particles. The powdered sodium tripolyphosphate then is slowly added and the mixture stirred until it is free-flowing. The sodium chloride is added and the composition stirred for 10 minutes to produce fragranced softening bath grains

What is claimed is:

1. A first dry fragrance composition for imparting a fragrance to a second particulate material through physical admixture, said first dry fragrance composition comprising (i) a nonabsorbent solid inorganic particulate substrate which is inert to said second particulate material and consisting essentially of sodium chloride, and (ii) from about 0.1 to about 30%, by weight of the composition, of a fragrance composition, said fragrance being deposited solely on the surface of the particulate substrate.

2. A dry fragrance composition according to claim 1 having from about 0.1 to about 10%, by total carrier weight, of said fragrance composition.

3. A dry fragrance composition according to claim 1 wherein the density and particle size of the nonabsorbent solid inorganic particulate substrate approximate the density and particle size of said second particulate material.

4. A dry fragrance composition according to claim 1 wherein the nonabsorbent solid inorganic particulate substrate has a mesh size of from about 400 to about 10.

5. A dry fragrance composition according to claim 1 wherein said fragrance composition contains a coloring agent.

6. A dry fragrance composition according to claim 4 wherein the color of coloring agent contrasts with the color of said second particulate material.

7. In a particulate material selected from the group consisting of laundry detergents, automatic dishwasher detergents, cat litter, bath salts, carpet cleaners, rug deodorizers, room deodorizers, fabric bleaches, and powdered cleaners, the improvement consisting of the uniform admixture therewith of a quantity of a dry fragrance composition having (i) a nonabsorbent solid inorganic particulate substrate which is inert to said particulate material and consisting essentially of sodium chloride, and (ii) from about 0.1 to about 30%, by weight of the composition, of a fragrance composition, said fragrance being deposited solely on the surface of the particulate substrate, said quantity being sufficient to impart said, fragrance to said particulate material.

8. The improvement according to claim 7 wherein the density and particle size of the nonabsorbent solid inorganic particulate substrate approximate the density and particle size of said particulate material.

9. The improvement according to claim 7 wherein said fragrance composition contains a coloring agent.

10. The improvement according to claim 9 wherein the color of coloring agent contrasts with the color of said particulate material.

* * * * *